(12) United States Patent
Liang et al.

(10) Patent No.: US 10,662,201 B2
(45) Date of Patent: May 26, 2020

(54) ALANTOLACTONE/ISOALANTOLACTONE SPIRO ARYL ISOXAZOLINE COMPOUNDS

(71) Applicants: Chengyuan Liang, Xi'an (CN); Xingke Ju, Xi'an (CN); Lei Tian, Xi'an (CN); Nan Qin, Tianjin (CN); Juan Xia, Zhanjiang (CN); Shaomeng Pei, Xi'an (CN); Han Li, Xi'an (CN); Yuzhi Liu, Xi'an (CN)

(72) Inventors: Chengyuan Liang, Xi'an (CN); Xingke Ju, Xi'an (CN); Lei Tian, Xi'an (CN); Nan Qin, Tianjin (CN); Juan Xia, Zhanjiang (CN); Shaomeng Pei, Xi'an (CN); Han Li, Xi'an (CN); Yuzhi Liu, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/167,590

(22) Filed: Oct. 23, 2018

(65) Prior Publication Data

US 2019/0185487 A1 Jun. 20, 2019

(30) Foreign Application Priority Data

Dec. 15, 2017 (CN) .......................... 2017 1 1346226

(51) Int. Cl.
*C07D 498/10* (2006.01)
*A61P 11/06* (2006.01)
*A61P 29/00* (2006.01)

(52) U.S. Cl.
CPC ............ *C07D 498/10* (2013.01); *A61P 11/06* (2018.01); *A61P 29/00* (2018.01)

(58) Field of Classification Search
CPC .................................................. C07D 489/10
USPC ........................................................ 514/379
See application file for complete search history.

*Primary Examiner* — Kevin E Weddington

(57) ABSTRACT

A compound of chemical formula I:

or chemical formula II:

or a pharmaceutical acceptable salt thereof is disclosed. $R_1$, $R_2$, $R_3$, and $R_4$ are independently H, halogen, nitro, hydroxyl, cyano, benzyloxy, $C_1$-$C_8$ straight or branched alkyl, C1-C8 straight or branched haloalkyl, $C_1$-$C_8$ straight or branched alkoxy.

8 Claims, No Drawings

ALANTOLACTONE/ISOALANTOLACTONE SPIRO ARYL ISOXAZOLINE COMPOUNDS

The present invention claims priority to Chinese Patent Application No. CN 201711346226.7, filed on Dec. 15, 2017, which is incorporated by reference for all purposes as if fully set forth herein.

FIELD OF THE INVENTION

The present invention relates to alantolactone/isoalantolactone spiro aryl isoxazoline compounds and a method of using the same.

BACKGROUND OF THE INVENTION

World Health Organization defines asthma as one of the major non-communicable diseases, and it is also a major hazard to human life and survival. In China, because of the frequent occurrence of large-scale smog, the number of asthma patients is increasing. Therefore, the development of new anti-asthma drugs has far-reaching social benefits. Asthma is clinically classified into episodes (acute episodes and chronic episodes) and remissions based on the symptoms and pathological features of asthma. The episodes and remissions alternate. Airway hyperresponsiveness and inflammation still exist during the remissions (Swedin L, Saarne T, Rehnberg M, et al. Patient stratification and the unmet need in asthma. Pharmacol Ther, 2017, 169: 13-34.). With the deepening understanding of the disease mechanism, the focus of asthma treatment has shifted from the simple relief of acute airway smooth muscle spasm to the comprehensive treatment of prevention and treatment of airway inflammation. Modern biomedical research indicates that asthma is inflammation caused by a variety of inflammatory cells and cytokines, especially chronic airway inflammation involving mast cells, eosinophils, T cells, and white blood cells. A variety of inflammatory factors including leukotrienes (LTC), interleukin (IL), and histamine are also involved.

Recent studies have found that the release of leukotrienes is one of the ultimate common pathways in a variety of different factors that cause inflammation and airway obstruction, having many different effects on the respiratory system. Leukotrienes are eicosanoid inflammatory mediators produced in leukocytes by the oxidation of arachidonic acid and the essential fatty acid eicosapentaenoic acid by the enzyme arachidonate 5-lipoxygenase (5-LO). The name leukotriene comes from the words leukocyte and triene. Studies have shown that $LTC_4$ has the strongest inflammatory activity among various leukotrienes (Schmidt D, Rabe K F., The role of leukotrienes in the regulation of tone and responsiveness in isolated human airways, Am J Respir Crit Care Med, 2000, 161 (2 Pt 2): 562-6.). Therefore, inhibition of $LTC_4$ production and blocking of $LTC_4$ binding to leukotriene receptors are important methods for the treatment of respiratory inflammation-related diseases including asthma and chronic obstructive pulmonary disease.

According to the Guidance of the Global Asthma Prevention and Control Initiative, inhibition of the leukotriene pathway can improve lung function and significantly improve bronchial asthma symptoms. Therefore, leukotriene modulators have been classified as drugs for controlling asthma symptoms and reducing seizures. The clinical efficacy of this class of drugs has been widely confirmed (Arakawa H, Hamasaki Y, Kohno Y, et al. Japanese guidelines for childhood asthma 2017. Allergol Int, 2017, 66(2): 190-204). Currently, there is only one anti-asthma drug based on inhibition of leukotriene production: ZILEUTON, a 5-lipoxygenase (5-LO) inhibitor. The development of novel leukotriene production inhibitors has broad application prospects and commercial value.

When studying the pharmacological activity of spiro aryl isoxazoline compounds, inventors found that the alantolactone/isoalantolactone spiro aryl isoxazoline compounds (as shown in Formulae I and II) can significantly inhibit the production of $LTC_4$ in the mast cell. Further studies found that the half-inhibitory concentration of representative compounds reaches 71.21 nM, which is the highest activity to inhibit $LTC_4$ production reported in the literature. Such compounds are lead compounds and drug candidates for anti-inflammatory and anti-asthmatic drug discovery based on the regulation of the leukotriene pathway.

SUMMARY OF THE INVENTION

In one embodiment, the present invention provides a compound of chemical formula I or II (an alantolactone/isoalantolactone spiro aryl isoxazoline compound):

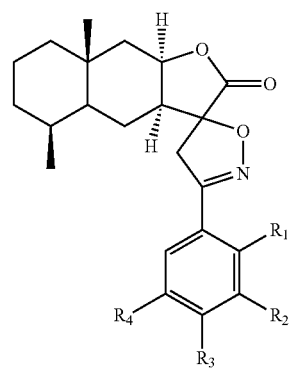

I

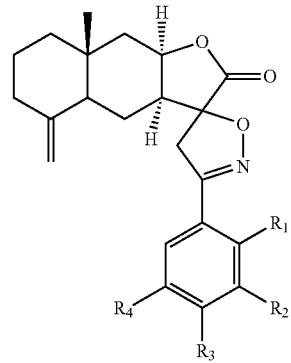

II or a pharmaceutical acceptable salt thereof. $R_1$, $R_2$, $R_3$, and $R_4$ are independently H, halogen, nitro, hydroxyl, cyano, benzyloxy, $C_1$-$C_8$ straight or branched alkyl, $C_1$-$C_8$ straight or branched haloalkyl, $C_1$-$C_8$ straight or branched alkoxy.

In another embodiment, in chemical formula I or II, $R_1$ is H, $R_2$ is F, $R_3$ is H, and $R_4$ is H.

In another embodiment, in chemical formula I or II, $R_1$ is H, $R_2$ is H, $R_3$ is F, and $R_4$ is H.

In another embodiment, in chemical formula I or II, $R_1$ is H, $R_2$ is H, $R_3$ is $CF_3$, and $R_4$ is H.

In another embodiment, in chemical formula I or II, $R_1$ is H, $R_2$ is H, $R_3$ is CN, and $R_4$ is H.

In another embodiment, in chemical formula I or II, $R_1$ is F, $R_2$ is H, $R_3$ is CN, and $R_4$ is H.

In another embodiment, in chemical formula I or II, $R_1$ is H, $R_2$ is $NO_2$, $R_3$ is F, and $R_4$ is H.

In another embodiment, in chemical formula I or II, $R_1$ is H, $R_2$ is CN, $R_3$ is H, and $R_4$ is F.

In one embodiment, the present invention provides a method of inhibiting leukotriene. The method includes administrating a therapeutically effective amount of the compound of chemical formula I or II to a subject.

In one embodiment, the present invention provides a method of treating asthma. The method includes administrating a therapeutically effective amount of the compound of chemical formula I or II to a subject.

In one embodiment, the present invention provides a method of treating inflammation. The method includes administrating a therapeutically effective amount of the compound of chemical formula I or II to a subject.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

The present invention provides an alantolactone/isoalantolactone spiro aryl isoxazoline compound or a pharmaceutical acceptable salt thereof. The compound has chemical formula I or II:

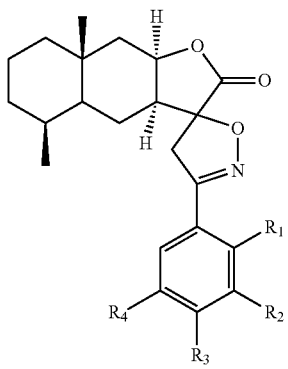

I

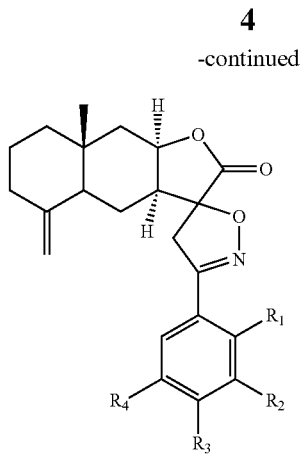

II

Alantolactone has the following structure:

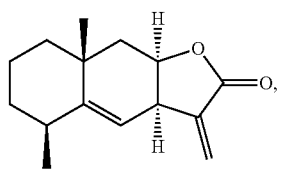 [SMILES: C=C1C(=O)O[C@@H]2C[C@@]3(C)CCC[C@H](C)C3=C[C@H]12]

and isoalantolactone has the following structure:

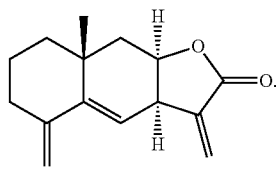 [SMILES: C=C1CCC[C@]2(C)C[C@H]3OC(=O)C(=C)[C@H]3C=C12]

In the chemical formula I or II, $R_1$, $R_2$, $R_3$, and $R_4$ can be the same or different. Preferably, $R_1$, $R_2$, $R_3$, and $R_4$ are independently H, halogen, nitro, hydroxyl, cyano, benzyloxy, $C_1$-$C_8$ straight or branched alkyl, $C_1$-$C_8$ straight or branched haloalkyl, $C_1$-$C_8$ straight or branched alkoxy. In formulas (I) and (II), the spiro carbon is a chiral atom. Compounds of formulas (I) and (II) may be separated into their individual diastereoisomers.

The compound of chemical formula I or II can be prepared in accordance with the following reaction scheme 1.

Scheme 1.

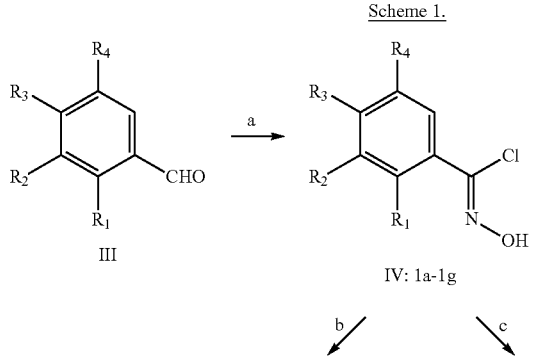

-continued

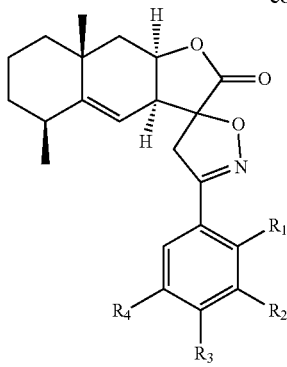

I: 2a-2g

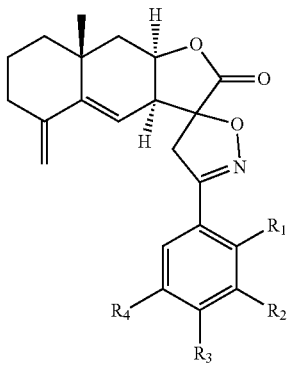

II: 3a-3g

Reagents and conditions: (a) 1) NCS, DMF, 40° C.; 2) NH₂OH•HCl, H₂O, r.t.; (b) Alantolactone, Et₃N, CH₂Cl₂, r.t.; (c) Isoalantolactone, Et₃N, CH₂Cl₂, r.t.

The substituents in formulae IV, I and II are listed in Table 1 below. The compounds of formula IV include compounds 1a-1g; the compounds of formula I include compounds 2a-2g; and the compounds of formula II include compounds 3a-3b.

TABLE 1

| Compounds | | | | |
|---|---|---|---|---|
| Compounds | $R_1$ | $R_2$ | $R_3$ | $R_4$ |
| 1a-3a | H | F | H | H |
| 1b-3b | H | H | F | H |
| 1c-2c | H | H | $CF_3$ | H |
| 1d-2d | H | H | CN | H |
| 1e-2e | F | H | CN | H |
| 1f-2f | H | $NO_2$ | F | H |
| 1g-2g | H | CN | H | F |

A second object of the present invention is to disclose the use of the compounds of formulas I and II in the field of anti-inflammatory and anti-asthmatic based on inhibition of leukotriene production. It is characterized in that the compounds inhibit the production of mast cells $LTC_4$. At the test concentrations, the inhibition rates of compounds 2a, 2b, 2c, 2f exceed 90%. In view of the important role of leukotrienes in the pathogenesis of inflammation and asthma, the above findings show the anti-inflammatory and anti-asthmatic application prospects of the compounds of formulas I and II.

Example 1: Preparation of Compounds 1a-1g

Aryl aldehyde (compound of formula III in Scheme 1) was dissolved in a mixture of acetonitrile and water (V/V=1:1) in a reaction flask, and hydroxylamine hydrochloride (1.1 equivalents) was added to the reaction flask at room temperature. The reaction was stirred at room temperature and monitored by thin layer chromatograph (TLC). When the reaction was complete, the solvent was removed under reduced pressure to obtain an intermediate. The intermediate was dissolved in dimethylformamide (DMF), and N-chlorosuccinimide (NCS) (1 equivalent) was added in portions to the DMF solution. The reaction solution was stirred at 40° C. and monitored by TLC. When the reaction was complete, ethyl acetate (20 times the reaction mixture) was added to dilute the reaction mixture, and the ethyl acetate solution was washed with water (5×20 mL). Ethyl acetate layer was collected, dried over $MgSO_4$, and concentrated to compounds 1a-1g. Compounds 1a-1g were used in the next step without purification.

Example 2: Preparation of Compounds 2a-2g

Compounds 1a-1g (0.16 mmol) were dissolved in 0.75 mL $CH_2Cl_2$ in a flask. Triethylamine ($Et_3N$) (0.13 mmol) and alantolactone (0.1 mmol) in 0.75 mL $CH_2Cl_2$ were then added. The reaction mixture was stirred at room temperature for 16 hours and monitored by TLC. When the reaction was complete, the reaction mixture was concentrated under reduced pressure to give crude products. The crude products were purified by silica column chromatography (eluting with PE:EA=6:1-3:1, v/v) to give compounds 2a-2g.

2.1

Compound 2a, colorless oil, yield 61.0%. $^1H$ NMR (400 MHz, $CDCl_3$): δ 7.47-7.39 (m, 3H), 7.14 (q, J=1.6 Hz, 1H), 5.15-5.14 (m, 1H), 5.11 (d, J=3.2 Hz, 1H), 3.64 (d, J=17.1 Hz, 1H), 3.50 (d, J=17.1 Hz, 1H), 3.12-3.10 (m, 1H), 2.52-2.49 (m, 1H), 2.21 (dd, J=3.24, 11.64 Hz, 1H), 1.90-1.79 (m, 1H), 1.66-1.51 (m, 4H), 1.49-1.42 (m, 1H), 1.24 (s, 3H), 1.14 (d, J=7.64 Hz, 3H). $^{13}C$ NMR (100 MHz, CDCl3): δ173.29, 163.25 (d, J=245.4 Hz), 155.68 (d, J=2.9 Hz), 154.06, 130.68 (d, J=8.14 Hz), 130.48 (d, J=12 Hz), 122.77 (d, J=3.1 Hz), 117.62 (d, J=21 Hz), 113.79 (d, J=23 Hz), 112.27, 90.37, 77.59, 43.04, 42.42, 42.14, 38.68, 36.65, 32.97, 32.67, 28.43, 22.81, 16.76.

2.2

Compound 2b, white solid, yield 63.0%. $^1H$ NMR (400 MHz, $CDCl_3$): δ 7.72-7.69 (m, 2H), 7.14-7.09 (m, 2H), 5.16-5.13 (m, 1H), 5.12 (d, J=3.2 Hz, 1H), 3.64 (d, J=17.0 Hz, 1H), 3.50 (d, J=17.0 Hz, 1H), 3.12-3.10 (m, 1H), 2.53-2.48 (m, 1H), 2.21 (dd, J=14.9, 3.4 Hz, 1H), 1.90-1.78 (m, 1H), 1.67-1.55 (m, 4H), 1.49-1.39 (m, 1H), 1.24 (s, 3H), 1.14 (d, J=7.6 Hz, 3H). $^{13}C$ NMR (100 MHz, $CDCl_3$): δ 173.36, 164.2 (d, J=250.1 Hz), 155.53, 153.96, 128.98 (d, J=8.6 Hz), 124.92 (d, J=3.2 Hz), 115.97 (d, J=21.91 Hz), 112.43, 90.15, 77.52, 43.09, 42.46, 42.15, 38.68, 36.89, 32.98, 32.83, 28.40, 22.79, 16.76.

2.3

Compound 2c, white solid, yield 58.0%. $^1H$ NMR (400 MHz, $CDCl_3$): δ 7.83-7.81 (m, 2H), 7.69-7.67 (m, 2H), 5.16-5.12 (m, 2H), 3.67 (d, J=17.2 Hz, 1H), 3.53 (d, J=17.2 Hz, 1H), 3.13 (s, 1H), 2.53-2.50 (m, 1H), 2.21 (dd, J=14.9, 3.4 Hz, 1H), 1.86-1.83 (m, 1H), 1.66-1.55 (m, 4H), 1.48-

1.45 (m, 1H), 1.24 (s, 3H), 1.14 (d, J=7.7 Hz, 3H). $^{13}$C NMR (100 MHz, CDCl$_3$): δ 173.18, 155.53, 154.19, 132.22 (d, J=32.0 Hz), 132.06 (d, J=32.4 Hz), 127.20, 125.77 (d, J=4.0 Hz), 123.72 (d, J=270.5 Hz), 112.16, 90.62, 43.02, 42.40, 42.13, 38.69, 36.47, 32.98, 32.81, 28.40, 22.79, 16.75.

2.4

Compound 2d, white solid, yield 70.0%. $^1$H NMR (400 MHz, CDCl$_3$): δ 7.82 (d, J=8.3 Hz, 2H), 7.72 (d, J=8.3 Hz, 2H), 5.17-5.16 (m, 1H), 5.11 (d, J=3.2 Hz, 1H), 3.65 (d, J=17.1 Hz, 1H), 3.50 (d, J=17.1 Hz, 1H), 3.14-3.12 (m, 1H), 2.53-2.48 (m, 1H), 2.22 (dd, J=15.0, 3.4 Hz, 1H), 1.90-1.80 (m, 1H), 1.67-1.55 (m, 4H), 1.49-1.44 (m, 1H), 1.42 (d, J=6.5 Hz, 1H), 1.25 (s, 3H), 1.14 (d, J=7.6 Hz, 3H). $^{13}$C NMR (100 MHz, CDCl$_3$): δ 173.0, 155.3, 154.4, 132.9, 132.6, 127.4, 118.1, 114.0, 112.0, 90.9, 77.6, 43.0, 42.4, 42.15, 38.7, 36.2, 33.0, 32.8, 28.4, 22.8, 16.76.

2.5

Compound 2e, white solid, yield 44.8%. $^1$H NMR (400 MHz, CDCl$_3$): δ 8.05-8.01 (m, 1H), 7.54-7.46 (m, 2H), 5.16-5.11 (m, 2H), 3.72 (d, J=17.8 Hz, 1H), 3.57 (d, J=17.9 Hz, 1H), 3.13-3.12 (m, 1H), 2.54-2.50 (m, 1H), 2.22 (dd, J=14.9, 3.4 Hz, 1H), 1.90-1.80 (m, 1H), 1.67-1.55 (m, 4H), 1.48-1.43 (m, 1H), 1.24 (s, 3H), 1.14 (d, J=7.6 Hz, 3H). $^{13}$C NMR (100 MHz, CDCl$_3$): δ 172.87, 160.83, 158.28, 154.35, 152.10 (d, J=3.1 Hz), 130.24 (d, J=3.5 Hz), 128.26 (d, J=3.6 Hz), 121.81 (d, J=11.6 Hz), 120.39 (d, J=25.6 Hz), 116.87, 115.34 (d, J=9.8 Hz), 111.97, 91.08, 42.94, 42.41, 42.14, 38.65, 32.98, 32.81, 28.37, 22.75, 16.75.

2.6

Compound 2f, yellow solid, yield 32.0%. $^1$H NMR (400 MHz, CDCl$_3$): δ 8.31 (d, J=6.76 Hz, 1H), 8.7 (m, 1H), 7.39 (t, J=9.48 Hz, 1H), 5.15 (m, 2H), 3.65 (d, J=17.08 Hz, 1H), 3.52 (d, J=17.12 Hz, 1H), 3.14 (m, 1H), 2.54 (m, 1H), 2.24 (dd, J=3.0, 11.8 Hz, 1H), 1.91-1.81 (m, 1H), 1.68-1.42 (m, 6H), 1.25 (s, 3H), 1.20-1.15 (m, 3H); $^{13}$C NMR (100 MHz, CDCl$_3$): δ 172.94, 157.79, 154.83 (d, J=55.0 Hz), 153.99, 133.58 (d, J=9.0 Hz), 126.07 (d, J=5.0 Hz), 124.55 (d, J=3.0 Hz), 119.39 (d, J=22.0 Hz), 111.86, 91.01, 42.89, 42.36, 42.15, 38.72, 36.37, 33.00, 32.81, 28.41, 22.82, 16.74.

2.7

Compound 2g, white solid, yield 51.0%. $^1$H NMR (400 MHz, CDCl$_3$): δ 7.75-7.70 (m, 2H), 7.44-7.43 (m, 1H), 5.17 (s, 1H), 5.10 (s, 1H), 3.62 (d, J=17.1 Hz, 1H), 3.48 (d, J=17.1 Hz, 1H), 3.13 (s, 1H), 2.54-2.50 (m, 1H), 2.22 (d, J=14.4 Hz, 1H), 1.87-1.81 (m, 1H), 1.67-1.55 (m, 4H), 1.49-1.39 (m, 1H), 1.24 (s, 3H), 1.14 (d, J=7.6 Hz, 3H). $^{13}$C NMR (100 MHz, CDCl$_3$): δ 172.74, 154.64, 132.58, 126.38, 120.73 (d, J=24.7 Hz), 118.34 (d, J=23.2 Hz), 111.81, 91.15, 42.90, 42.39, 42.16, 38.73, 36.11, 33.02, 32.81, 28.37, 22.79, 16.74.

Example 3: Preparation of Compounds 3a-3b

Compounds 1a-1b (0.16 mmol) were dissolved in 0.75 mL CH$_2$Cl$_2$ in a flask. Triethylamine (Et$_3$N) (0.13 mmol) and isoalantolactone (0.1 mmol) in 0.75 mL CH$_2$Cl$_2$ were then added. The reaction mixture was stirred at room temperature for 16 hours and monitored by TLC. When the reaction was complete, the reaction mixture was concentrated under reduced pressure to give crude products. The crude products were purified by silica column chromatography (eluting with PE:EA=6:1-3:1, V/V) to give compounds 3a-3b.

3.1

Compound 12a, white solid, yield 54.0%. $^1$H NMR (400 MHz, CDCl$_3$): δ 7.46-7.37 (m, 3H), 7.16-7.12 (m, 1H), 5.00 (s, 1H), 4.81 (s, 1H), 4.46 (s, 1H), 3.72 (d, J=8.5 Hz, 1H), 3.41 (d, J=8.52 Hz, 1H), 2.56 (t, J=6.26 Hz, 1H), 2.36-2.25 (m, 2H), 2.04-1.97 (m, 1H), 1.88 (d, J=6.16 Hz, 1H), 1.69-1.51 (m, 6H), 1.29-1.23 (m, 1H), 1.16-1.07 (m, 1H), 0.80 (s, 3H); $^{13}$CNMR (100 MHz, CDCl$_3$): δ173.45, 163.27 (d, J=245.8 Hz), 155.54, 148.88, 130.68, 130.49 (d, J=8.1 Hz), 122.72 (d, J=2.96 Hz), 117.65 (d, J=21.21 Hz), 113.77 (d, J=23.1 Hz), 106.57, 91.17, 78.24, 46.37, 43.30, 41.96, 41.15, 36.69, 36.20, 34.44, 22.60, 21.34, 17.79.

3.2

Compound 3b, white solid, yield 67.2%. $^1$H NMR (400 MHz, CDCl$_3$): δ 7.71-7.68 (m, 2H), 7.14-7.09 (m, 2H), 5.00 (brs, 1H), 4.81 (s, 1H), 4.46 (s, 1H), 3.73 (d, J=17.0 Hz, 1H), 3.42 (d, J=17.0, 1H), 2.59-2.53 (m, 1H), 2.37-2.33 (m, 1H), 2.27 (dd, J=15.6, 1.2 Hz, 1H), 2.05-1.97 (m, 1H), 3.42 (d, J=12.3, 1H), 1.70-1.52 (m, 5H), 1.41 (t, J=7.3 Hz, 1H), 1.30-1.23 (m, 1H), 1.12 (q, J=5.4, 1H), 0.81 (s, 3H). $^{13}$C NMR (100 MHz, CDCl$_3$): δ 173.62, 163.9 (d, J=250.1 Hz), 155.43, 148.91, 128.94 (d, J=8.6 Hz), 124.83 (d, J=3.4 Hz), 116.07 (d, J=21.9 Hz), 112.43, 106.54, 90.95, 78.26, 46.35, 45.80, 43.29, 41.93, 41.14, 36.68, 36.42, 34.43, 22.59, 21.36, 17.78.

Example 4: Inhibitory Effect of the Compounds on Leukotriene C4 (LTC4) Production in Mouse Bone Marrow-Derived Mast Cells (BMMCs)

4.1 Extraction of BMMCs (1) Experimental Animal: a 6-week-old female Balb/C mouse without specific pathogens.

(2) Extraction Process: the mouse was sacrificed by cervical dislocation. After confirming the death of the mouse, it was immersed in alcohol for 3-5 minutes. The back skin of the mouse was cut with tweezers and scissors on a clean bench. The spleen was removed and placed in a filter. The filter was placed in a petri dish containing serum-free medium. The spleen was grounded into a cell suspension having a cell concentration of 2×10$^6$ cells/mL. 2.5 µg/mL of lectins was added, and cell suspension was then cultured in RPMI1640 medium for 5 days. The supernatant was collected. The femur bone of the mouse was removed, and joints of the bone were cut. The bone marrow was washed into a centrifuging tube by using serum-free medium. The bone marrow containing medium was then centrifuged, and the supernatant was discarded and the pellet was red bone marrow.

(3) Cell Culture: The cells were cultured for 4 weeks with RPMI1640, 10% Gibco FBS, 20% spleen supernatant, 1% AEPS, 1% MEM, and 1% double antibody.

4.2 MTT Assay to Determine the Non-Cytotoxic Concentration of Compounds (1) Preparation of MTT Solution: 5 mg/mL MTT solution was prepared by weighing an amount of MTT ((2-(4,5-dimethyl-2-thiazolyl)-3,5-diphenyl-2H-tetrazole hydrobromide) and dissolving MMT in PBS (solvent), and the solution was then filtered using a 0.22 m microporous membrane. The solution was light yellow and stored at −20° C.

(2) Method: BMMCs were seeded in 96-well plates at a density of 2×10$^5$/mL at 100 µL per well, and the compounds of different concentrations were added. 100 µL culture medium and 100 µL PBS were used as blank control. After 7 hours, 20 µL MMT (5 mg/mL) was added to each well. The plates were then placed in an incubator (5% CO$_2$, 37° C.) for 4 hours. After the reaction was complete, the supernatant was discarded, and 150 µL of DMSO was added to each well. After mixing, the absorbance (OD value) was measured at 490 nm using a microplate reader.

$$\text{Cell Viability} = (OD_{compounds} - OD_{culture\ medium}) / (OD_{PBS} - OD_{culture\ medium}) \times 100\%$$

The inhibition rates on the growth of BMMCs of the compounds at 10 µM are shown in Table 2.

TABLE 2

Inhibition of the Growth of BMMCs by the Compounds (10 µM)

| Compounds | Cell Toxicity (%) |
|---|---|
| 2a | 1.81 |
| 2b | 1.25 |
| 2c | 1.82 |
| 2d | 1.98 |
| 2e | 3.41 |
| 2f | 2.33 |
| 2g | 1.01 |
| 3a | 2.35 |
| 3b | 1.99 |

4.3 Effects of the Compounds on the Release of Inflammatory Factor $LTC_4$ from BMMCs Principle: This experiment is based on the competitive binding of $LTC_4$ to the LTC4-acetylcholinesterase conjugate ($LTC_4$ tracer) to determine the amount of LTC4 antiserum. Because the concentration of the $LTC_4$ tracer is constant and the concentration of $LTC_4$ is varied, the amount of $LTC_4$ tracer bound to the $LTC_4$ antiserum is inversely proportional to the amount of $LTC_4$. The antibody-$LTC_4$ complex binds to the murine monoclonal anti-rabbit IgG, while the murine monoclonal anti-rabbit IgG has previously been conjugated to the kit. After the reaction system was stabilized, the unbound reagent was washed away. Ellman's reagent (a substrate containing acetylcholinesterase) was added. The enzymatic reaction had a distinct yellow reaction, strong absorption at 405 nm. The color depth was measured by the spectrophotometric method, and is proportional to the amount of $LTC_4$ tracer, which is inversely proportional to the amount of $LTC_4$.

(2) Methods:

(a) Sample Preparation: culturing mature BMMCs, adding IgE overnight, washing with PBS three times, and then spreading in 96-well plates ($1\times10^6$ cells/well). The test compound solutions were added to plates and the plates were incubated for 1-1.5 hours, stimulating with DNP-HSA for 15 min. The solutions were then centrifuged at 3000 rpm for 3 min at 4° C., and the supernatant was collected and diluted 5-fold with RPMI 1640 to obtain sample solution.

(b) ELISA Kit Reaction: Adding reagents according to the kit instructions, reacting at 4° C. for 18 h, and washing with washing buffer. 200 µL of Ellman's reagent was added to each well, reacting for 40 min.

(c) Measurement of Absorbance: The absorbance was measured at 405 nm.

(3) Results:

The inhibition rates of the compounds for the production of $LTC_4$ by BMMCs at a concentration of 10 µM are shown in Table 3. Further, a concentration-dependent study of the compound 2b was carried out, and the half-inhibitory concentration ($IC_{50}$) was calculated to be 71.21 nM.

TABLE 3

Inhibition Rate (%) of the Compounds on $LTC_4$ production by BMMCs (10 µM)

| Compounds | Inhabitation Rate (%) |
|---|---|
| 2a | 95.2 |
| 2b | 97.5 |
| 2c | 94.2 |
| 2d | 37.7 |
| 2e | 74.1 |
| 2f | 85.2 |
| 2g | 77.2 |
| 3a | 70.1 |
| 3b | 73.4 |

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound of chemical formula I or II:

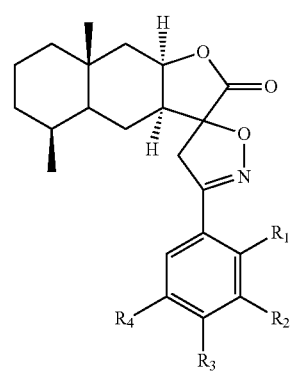

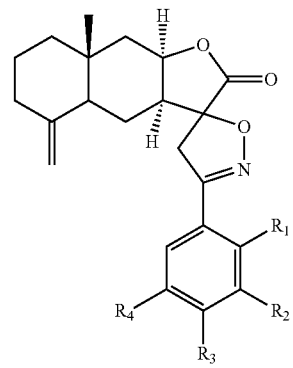

or a pharmaceutical acceptable salt thereof, wherein $R_1$, $R_2$, $R_3$, and $R_4$ are independently H, halogen, nitro, hydroxyl, cyano, benzyloxy, $C_1$-$C_8$ straight or branched alkyl, $C_1$-$C_8$ straight or branched haloalkyl, $C_1$-$C_8$ straight or branched alkoxy.

2. The compound of claim 1, wherein $R_1$ is H, $R_2$ is F, $R_3$ is H, and $R_4$ is H.

3. The compound of claim 1, wherein $R_1$ is H, $R_2$ is H, $R_3$ is F, and $R_4$ is H.

4. The compound of claim 1, wherein $R_1$ is H, $R_2$ is H, $R_3$ is $CF_3$, and $R_4$ is H.

5. The compound of claim 1, wherein $R_1$ is H, $R_2$ is H, $R_3$ is CN, and $R_4$ is H.

6. The compound of claim 1, wherein $R_1$ is F, $R_2$ is H, $R_3$ is CN, and $R_4$ is H.

7. The compound of claim 1, wherein $R_1$ is H, $R_2$ is $NO_2$, $R_3$ is F, and $R_4$ is H.

8. The compound of claim 1, wherein $R_1$ is H, $R_2$ is CN, $R_3$ is H, and $R_4$ is F.

* * * * *